(12) United States Patent
Waimer et al.

(10) Patent No.: US 10,028,986 B2
(45) Date of Patent: Jul. 24, 2018

(54) METHOD FOR PRODUCING GINKGO EXTRACTS

(71) Applicant: Dr. Willmar Schwabe GMBH & Co., KG, Karlsruhe (DE)

(72) Inventors: Frank Waimer, Karlsruhe (DE); Steffen Reinhard, Karlsruhe (DE); Hermann Hauer, Karlsruhe (DE)

(73) Assignee: Dr. Willmar Schwabe GMBH & Co., KG, Karlsruhe (DE)

( * ) Notice: Subject to any disclaimer, the term of this patent is extended or adjusted under 35 U.S.C. 154(b) by 162 days.

(21) Appl. No.: 15/117,965

(22) PCT Filed: Jan. 12, 2015

(86) PCT No.: PCT/EP2015/050401
§ 371 (c)(1),
(2) Date: Aug. 10, 2016

(87) PCT Pub. No.: WO2015/117793
PCT Pub. Date: Aug. 13, 2015

(65) Prior Publication Data
US 2016/0367612 A1    Dec. 22, 2016

(30) Foreign Application Priority Data
Feb. 10, 2014  (DE) .................. 10 2014 202 318

(51) Int. Cl.
*A61K 36/16* (2006.01)

(52) U.S. Cl.
CPC .......... *A61K 36/16* (2013.01); *A61K 2236/00* (2013.01); *A61K 2236/39* (2013.01)

(58) Field of Classification Search
None
See application file for complete search history.

(56) References Cited

U.S. PATENT DOCUMENTS

| 5,322,688 A * | 6/1994 | Schwabe ............. A61K 31/365 424/752 |
| 5,389,370 A | 2/1995 | O'Reilly et al. |
| 8,642,099 B2 | 2/2014 | Erdelmeier et al. |
| 2006/0251745 A1 | 11/2006 | Erdelmeier et al. |
| 2006/0251746 A1 | 11/2006 | Erdelmeier et al. |
| 2008/0193572 A1 | 8/2008 | Carite et al. |
| 2008/0286391 A1 | 11/2008 | Erdelmeier et al. |

FOREIGN PATENT DOCUMENTS

| DE | 39 40 092 A1 | 6/1991 |
| DE | 39 40 094 C2 | 7/1992 |
| DE | 10 2005 061948 A1 | 11/2006 |
| EP | 0 360 556 B1 | 4/1993 |
| EP | 0 431 535 B1 | 3/1994 |
| EP | 0 431 536 B1 | 7/1995 |
| EP | 1 868 625 B1 | 7/2008 |
| EP | 1 868 568 B1 | 10/2008 |
| JP | 03279332 A | 12/1991 |
| WO | 2006/117169 A1 | 11/2006 |
| WO | 2006 117171 A1 | 11/2006 |
| WO | 2012/146592 A1 | 11/2012 |

OTHER PUBLICATIONS van Beek et al., "Chemical analysis and quality control of Ginkgo biloba leaves, extracts, and phytopharmaceuticals", Journal of Chromatography A, 2009, vol. 1216, pp. 2002-2032.
International Search Report—PCT/EP2015/050410, dated Feb. 10, 2014.
Deng, et al., Journal of Chromatography A, 986 (2003) 121-127, XP4401771.
European pharmacopoeia (version 8.0; monograph Apr. 2008: 1827—"Ginkgo dry extract, refined and quantified".
Notification for the approval and registratin od frugs (preparation monographs for the human medicine area)—Ginko Folium (Ginkgo biloba leaves), Bundesanzeiger 46, (133), 7360-7361 (1994).

* cited by examiner

*Primary Examiner* — Christopher R Tate
*Assistant Examiner* — Russell G Fiebig
(74) *Attorney, Agent, or Firm* — Mintz Levin Cohn Ferris Glovsky and Popeo, P.C.; Peter F. Corless

(57) ABSTRACT

The present invention relates to an improved multistep method for the production of an extract of *Ginkgo biloba* leaves for use as a drug.

10 Claims, No Drawings

METHOD FOR PRODUCING GINKGO EXTRACTS

This application is a National Phase application filed under 35 U.S.C. § 371 of PCT International Application No. PCT/EP2015/050401 with an International Filing Date of Jan. 12, 2015, which claims under 35 U.S.C. § 119(a) the benefit of German Application No. 10 2014 202 318.1, filed Feb. 10, 2014, the entire contents of which are incorporated herein by reference.

The present invention relates to an improved multistep method for the production of an extract of *Ginkgo biloba* leaves for use as a drug.

Extracts from *Ginkgo biloba* leaves have been used for centuries as drugs. Currently they are used for the treatment of various kinds of dementia and its symptoms and of cerebral and peripheral circulatory disorders. Ingredients the activity is related to are terpene lactone (ginkgolides A, B, C and bilobalide) and glycosides of flavones (quercetin, kaempherol and isorhamnetin). According to the current European pharmacopoeia (version 8.0; monograph April 2008: 1827 "*Ginkgo* dry extract, refined and quantified") which is binding for all *Ginkgo* extracts but can be approved as drugs in the scope of the pharmacopoeia, *Ginkgo* extract contains 22.0% to 27.0% flavonoids, calculated as flavonglycosides, 2.6% to 3.2% bilobalide, 2.8% to 3.4% ginkgolides A, B and C and not more than 5 ppm ginkgolic acids. The preparation is described as follows in the "Bekanntmachung über die Zulassung und Regis-trierung von Arzneimittel (Aufbereitungsmonographien für den humanmedizinischen Bereich)—*Ginkgo folium* (*Ginkgo-biloba*-Blätter)" ("notification for the approval and registration of drugs (preparation monographs for the human medicine area)—*Ginkgo folium* (*Ginkgo biloba* leaves)") (Bundesanzeiger 46, (133), 7360-7361 (1994)): "A dry extract prepared from the dried leaves of *Ginkgo biloba* LINNE with acetone-water and subsequent purification steps without the addition of concentrates or isolated ingredients".

Recently, *Ginkgo* leaves with contents of ingredients are increasingly obtained which upon extraction with the known method do not lead to extracts according to the requirements of the European pharmacopoeia. In particular, currently *Ginkgo* leaves with unusual high amounts of terpene lactones are increasingly harvested resulting in accordingly increased contents in the extract. However, occasionally *Ginkgo* leaves also contain an unusually high amount of flavonoids.

The most important extraction methods resulting in extracts according to the requirements of the Ph. Eur. when appropriate *Ginkgo* leaves are used, are described in EP 431535 B1 (Dr. Willmar Schwabe GmbH & Co.) and in EP 360556 B1 (Indena S.p.A.). Recently, the method according to EP 431536 B1 (Dr. Willmar Schwabe GmbH & Co.) has become more important since in this method no toxicologically critical compounds like lead salts (EP 431535 B1) or aromatic hydrocarbons (EP 360556 B1) are required.

According to claim 1 of EP 431536 B1, the claimed method for the production of an extract of *Ginkgo biloba* leaves is characterised by (a) fresh or dried green leaves of *Ginkgo biloba* are extracted with acetone containing water, an alkanol with 1 to 3 C atoms containing water or anhydrous methanol at a temperature of about 40 to 100° C., (b) the major amount of the organic solvent is separated from the extract to a content of not more than 10% by weight, wherein in the last distillation steps water is added, if necessary, (c) the remaining concentrated aqueous solution is diluted with water to a solid content of 5 to 25% by weight, cooled to a temperature below 25° C. while stirring, left till the formation of a precipitate, and the formed precipitate consisting of the lipophilic components poorly soluble in water is separated, (d) ammonium sulfate is added to the remaining aqueous solution and the formed solution is extracted with methyl ethyl ketone or a mixture of methyl ethyl ketone and acetone, (e) the obtained extract is concentrated to a solid content of 50 to 70% and the obtained concentrate is diluted with water to a solid content of 5 to 20%, (f) the such obtained solution is extracted in multiple steps with a butanol or pentanol not miscible with water, (g) the butanol and pentanol phases, respectively, are concentrated to a solid content of 50 to 70%, (h) the concentrate is diluted by the addition of such amounts of water and ethanol that a solution with 5 to 20% by weight dry extract in 20 to 60% by weight aqueous ethanol is obtained, (i) the aqueous alcoholic solution is extracted with an aliphatic or cycloaliphatic solvent having a boiling point of 60 to 100° C. for the further separation of alkyl phenol compounds, (j) the water phase is concentrated under reduced pressure and is dried at a temperature of not more than 60 to 80° C. to a dry extract having a water content of less than 5%.

The object of the present invention is to provide an improved method for the production of an extract of leaves of *Ginkgo biloba* which fulfils the requirement of the Ph. Eur. even if *Ginkgo* leaves with an unfavourable spectrum of ingredients, in particular with increased contents of terpene lactons, but also with an increased content of flavonoids are used. Further, it is the object of the present invention to perform the method in such manner that no pure compounds or nearly pure concentrates are added since this is not allowed for *Ginkgo* extracts used as drugs.

Surprisingly, it has been found that by additional method steps in the method according to EP 431 536 B1 also from *Ginkgo* leaves with an unfavourable spectrum of ingredients, extracts according to the European pharmacopoeia can be obtained. For this purpose, after the extraction (liquid liquid distribution) according to step (d), the aqueous phase is separated from the methyl ethyl ketone and methyl ethyl ketone-acetone phase, respectively, the methyl ethyl ketone and methyl ethyl ketone-acetone phase, respectively, it concentrated to a dry extract portion of 40 to 80% by weight to obtain a concentrate. A portion of 10 to 60% by weight of the concentrate is adjusted with water and methyl ethyl ketone to a dry extract portion of not more than 60% by weight and a methyl ethyl ketone content of not more than 30% by weight, and is extracted with a mixture of methyl ethyl ketone and an aliphatic solvent having a boiling point of 60 to 100° C. in a ratio of 7/3 to 9/1 (m/m) to obtain a water-methyl ethyl ketone phase and a methyl ethyl ketone-aliphatic solvent phase.

The water-methyl ethyl ketone phase is combined with the remaining 90 to 40% by weight of the concentrate to obtain a solution and thereby, to counteract a too high content of terpene lactones in the final product.

Alternatively, the obtained methyl ethyl ketone-aliphatic solvent phase can be combined with the remaining 90 to 40% by weight of the concentrate to counteract a too high content of flavonoides in the final product.

Therefore, the method according to the invention for producing a dry extract of *Ginkgo biloba* leaves having a content of 22.0% by weight to 27.0% by weight flavonoids, calculated as flavon glycosides, 2.6% by weight to 3.2% by weight bilobalide, 2.8% by weight to 3.4% by weight ginkgolides A, B and C and not more 5 ppm ginkgolic acids, comprises the following steps:

(a) extraction of fresh or dried green leaves of *Ginkgo biloba* with acetone containing water, an alkanol with 1 to 3 C atoms containing water or anhydrous methanol at a temperature of about 40 to 100° C. to obtain a crude extract solution, (b) separating by distillation the major amount of the acetone or alkanol with 1 to 3 C atoms from the crude extract solution of step (a) to a content of not more than 10% by weight, wherein, if anhydrous methanol is used in step (a), water is added at the last distillation steps to obtain a concentrated aqueous solution, (c) diluting the concentrated aqueous solution of step (b) with water to a solid content of 5 to 25% by weight, cooling to a temperature below 25° C., keeping cool until the formation of a precipitate and separating the formed precipitate to obtain an aqueous solution again, (d) adding ammonium sulfate to the obtained aqueous solution of step (c) and extraction of the formed solution containing ammonium sulfate with methyl ethyl ketone or a mixture of methyl ethyl ketone and acetone, separating the aqueous phase from the methyl ethyl ketone or methyl ethyl ketone-acetone phase to obtain a methyl ethyl ketone or methyl ethyl ketone-acetone phase, (e) concentrating the methyl ethyl ketone or methyl ethyl ketone-acetone phase of step (d) to a dry extract portion of 40 to 80% by weight to obtain a concentrate, (f) adjusting a portion of 10 to 60% by weight of the concentrate of step (e) with water and methyl ethyl ketone to a dry extract portion of not more than 60% by weight and a methyl ethyl ketone content of not more than 30% by weight to obtain an adjusted extraction solution and extraction of the obtained adjusted extraction solution with a mixture of methyl ethyl ketone and an aliphatic solvent having a boiling point of 60 to 100° C. in a ratio of 7/3 to 9/1 (m/m) to obtain a water-methyl ethyl ketone phase and a methyl ethyl ketone-aliphatic solvent phase, (g) combining the remaining portion of 90 to 40% by weight of the concentrate of step (e) with the water-methyl ethyl ketone phase of step (f) or the methyl ethyl ketone-aliphatic solvent phase of step (f) to obtain a solution, (h) concentrating the solution of step (g) to a solid content of 50 to 70% by weight and diluting the obtained concentrate with water to a solid content of not more than 50% by weight to obtain a solution, (i) multistep extraction of the solution obtained in step (h) with a butanol or pentanol not miscible with water to obtain a butanol or pentanol phase, (j) concentrating the butanol or pentanol phase of step (i) to a solid content of at least 50% by weight to obtain a concentrate, (k) diluting the concentrate obtained in step (j) by the addition of such amounts of water and ethanol, if necessary, that a solution with 5 to 20% by weight dry extract in water or not more than 60% by weight aqueous ethanol is obtained, (l) extraction of the aqueous or aqueous ethanolic solution of step (k) with an aliphatic solvent having a boiling point of 60 to 100° C., separating the aqueous phase from the aliphatic solvent phase to obtain a water phase, (m) concentrating the water phase obtained in step (l) under reduced pressure and at a temperature of not more than 60 to 80° C. to obtain a dry extract with a water content of less than 5% by weight.

In preferred embodiments of the invention, as extraction solvent in step (a), acetone containing water having an acetone content of about 50 to 70% by weight, particularly preferred having an acetone content of about 60% by weight, is used, as extraction solvent in step (a), an alkanol containing water, selected from methanol, ethanol, 1-propanol and 2-propanol, having an alkanol content of about 50% by weight to 70% by weight, particularly preferred ethanol containing water having an ethanol content of about 60% by weight, is used, in step (c), the diluted active solution is cooled to a temperature below 12° C., in step (d), at least 30% by weight ammonium sulfate, particularly preferred 30 to 50% by weight ammonium sulfate, with respect to the aqueous solution of step (c) is added, in step (d), it is extracted with a mixture of methyl ethyl ketone and acetone in a ratio of 7/3 to 3/4 (m/m), in step (i), it is extracted with 1-butanol and/or in step (l), it is extracted with heptane, particularly preferred with n-heptane or a mixture of heptane isomers having a portion of more than 35% by weight of n-heptane.

Furthermore, in analogy to EP 1868625 B1 and EP 1868568 B1, the following supplementary method steps for removing 4-O-methylpyridoxine can be performed:

(n) preparing an aqueous ethanolic *Ginkgo* extract solution having an ethanol content of 40% by weight to 60% by weight from the water phase of step (k) or from the dry extract of step (m), (o) applying the aqueous ethanolic *Ginkgo* extract solution of step (n) on a strongly acidic ion exchanger to remove 4'-O-methyl pyridoxine which remains at the ion exchanger and eluating using aqueous ethanol to obtain an extraction solution free of 4-O-methyl pyridoxine as eluate, (p) concentrating the eluate of step (o) under reduced pressure and drying at a temperature of not more than 60 to 80° C. to a dry extract having a water content of less than 5% by weight.

Examples for strongly acidic ion exchangers are Merck I and Amberlite IR-120. Typically, the strongly acidic ion exchanger is a polystyrene resin to which sulfonic acid groups are bound.

In the following, some definitions of terms used in connection with the method according to the invention are stated:

dry extract: dry extracts have in general a water content of not more than 5% by weight according to the European pharmacopoeia.

The reference to anhydrous, for example in connection with the anhydrous methanol in step (a), refers in connection with the present invention to a water content of ≤1% by weight of water.

Extraction comprises one-step, multistep and continuous extraction.

The aliphatic solvents having a boiling point of 60 to 100° C. are preferably n-heptane or mixtures of saturated acyclic and/or cyclic aliphatic hydrocarbons which are defined by their boiling point and are known and commercially available under the designation petroleum ether or petroleum gasoline. Preferably, a mixture of aliphatic hydrocarbons is used, consisting essentially of n-heptane and other C7 alkanes. A high portion of n-heptane of more than 35% by weight n-heptane (boiling point 98° C.) is found for instance in the fraction 94-100° C.

The butanol or pentanol not miscible with water mentioned in step (i) is preferably 1-butanol or 1-pentanol.

In the following, the method according to the invention is further explained and described by Comparative Example 1 according to EP 431 536 B1 and Example 1 according to the invention.

STARTING SOLUTION FOR EXAMPLE 1 AND COMPARATIVE EXAMPLE 1

(According to the Method Steps (a) to (d) of EP 431 536 B1 and the Method According to the Invention)

In the following examples, the term "heptane" means a mixture of saturated aliphatic hydrocarbons having a boiling range of 94-100° C. and a portion of n-heptane of more than 35% by weight.

500 g dried and crushed leaves of *Ginkgo biloba* were extracted with 3.75 kg 60% by weight acetone for 30 min at 60° C. The plant material was filtered, extracted again with 3.75 kg 60% by weight acetone 30 min at 60° C. and filtered again. The such obtained two extract solutions were combined and concentrated (438 g; dry extract portion 36.9%).

The resulting concentrate was diluted with 400 g water and stirred for 1 h at 12° C. The formed precipitate was filtered and 240 g ammonium sulfate were added to the filtrate and dissolved. This solution was extracted twice with each 400 ml methyl ethyl ketone/acetone 6/5 (m/m). The methyl ethyl ketone/acetone phases were combined (808 g).

COMPARATIVE EXAMPLE 1 ACCORDING TO EP 431536 B1

(According to Method Steps (e) to (j))

Half of the above starting solution (404 g) was concentrated (27.2 g); dry extract portion (50%). This concentrate was diluted with 107.8 g water (dry extract portion 10%) and extracted by shaking three times with each 65 ml 1-butanol saturated with water. The 1-butanol phases were combined, concentrated and dried in vacuo for 16 h at 50° C. (6.72 g).

The dry extract such obtained was dissolved in a mixture of 20.2 g ethanol and 40.3 g water (dry extract portion 10%). This solution was extracted by shaking three times with each 20 ml heptane, concentrated and dried in vacuo for 16 h at 50° C.: 6.11 g (2.4% with respect to the drug).

|  | Found | Ph. Eur. |
|---|---|---|
| Flavonoids | 23.62% | 22.0-27.0% |
| Bilobalide | 5.48% | 2.6-3.2% |
| Ginkgolides A, B and C | 5.29% | 2.8-3.4% |
| Ginkgolic acids | <5 ppm | max. 5 ppm |

The extract such obtained does not meet with the requirements of the European pharmacopoeia with respect to the contents of bilobalide and ginkgolides A, B and C.

EXAMPLE 1 ACCORDING TO THE INVENTION (According to the Method Steps (e) to (m) of the Invention)

The second half of the above starting solution (404 g) was concentrated (20.5 g; dry extract portion 68.2%). 10.75 g of this concentrate were adjusted with 8.1 g water and 5.6 g methyl ethyl ketone to a dry extract portion of 30% and a methyl ethyl ketone content of 23% by weight, and were extracted by shaking twice with each 18.3 g methyl ethyl ketone/heptane 8/2 (m/m).

The water-methyl ethyl ketone phase was combined with the remaining concentrate of starting solution (9.75 g). This solution was concentrated to 24.17 g, adjusted with 115.5 g water to a dry extract portion of 10% and extracted by shaking three times with each 65 ml 1-butanol saturated with water. The 1-butanol phases were combined, concentrated and dried in vacuo for 16 h at 50° C. (5.93 g).

The dry extract such obtained was dissolved in a mixture of 17.8 g ethanol and 35.6 g water (dry extract portion 10%). This solution was extracted by shaking three times with each 20 ml heptane, concentrated and dried in vacuo for 16 h at 50° C.: 5.29 g (2.1% with respect to the drug).

|  | Found | Ph. Eur. |
|---|---|---|
| Flavonoids | 25.95% | 22.0-27.0% |
| Bilobalide | 3.01% | 2.6-3.2% |
| Ginkgolides A, B and C | 3.06% | 2.8-3.4% |
| Ginkgolic acids | <5 ppm | max. 5 ppm |

The extract such obtained needs the requirements of the European pharmacopoeia with respect to all contents, in particular the contents of bilobalide and ginkgolides A, B and C.

The invention claimed is:

1. A method for producing a dry extract of *Ginkgo biloba* leaves, comprising the following steps:
    (a) extracting fresh or dried green leaves of *Ginkgo biloba* at a temperature of about 40 to 100° C. with an extract solvent selected from the group consisting of aqueous acetone, an aqueous alkanol of 1 to 3C-atoms, and anhydrous methanol to obtain a crude extract solution;
    (b) vacuum distilling the crude extract solution from step (a) to remove the extract solvent to a maximum content of 10% by weight to obtain a concentrated aqueous solution, wherein, if anhydrous methanol is used in step (a), water is added at the last distillation step;
    (c) diluting the concentrated aqueous solution of step (b) with water to a solids content of 5 to 25% by weight, cooling to a temperature below 25° C., keeping cool until the formation of a precipitate and separating the formed precipitate to obtain a diluted aqueous solution;
    (d) adding ammonium sulfate to the diluted aqueous solution of step (c) to a concentration of at least 30% by weight and extracting said solution with an extraction solvent selected from a methyl ethyl ketone or a mixture of methyl ethyl ketone and acetone, separating the aqueous phase from the methyl ethyl ketone or methyl ethyl ketone-acetone phase to obtain a methyl ethyl ketone or methyl ethyl ketone-acetone phase;
    (e) concentrating the methyl ethyl ketone or methyl ethyl ketone-acetone phase of step (d) to a solids content of 40 to 80% by weight to obtain a concentrate;
    (f) separating the concentrate of step (e) into a first and second portion, wherein the first portion is 10 to 60% by weight of the concentrate of step (e), adding water and methyl ethyl ketone to said first portion to produce an adjusted extraction solution with a solids content of not more than 60% by weight and a methyl ethyl ketone content of not more than 30% by weight, and extracting said adjusted extraction solution with a mixture of methyl ethyl ketone and an aliphatic solvent having a boiling point of 60 to 100° C. in a ratio of 7/3 to 9/1

(m/m) to obtain a water-methyl ethyl ketone phase and a methyl ethyl ketone-aliphatic solvent phase;

(g) combining the second portion of the concentrate of step (e) with the water-methyl ethyl ketone phase or the methyl ethyl ketone-aliphatic solvent phase of step (f) to obtain a solution;

(h) concentrating the solution of step (g) to a solids content of 50 to 70% by weight and diluting the obtained concentrate with water to a solid content of not more than 50% by weight to obtain a solution;

(i) multiply extracting the solution obtained in step (h) with butanol or pentanol as an extraction solvent to obtain a butanol or pentanol phase;

(j) concentrating the butanol or pentanol phase of step (i) to a solid content of at least 50% by weight to obtain a concentrate;

(k) diluting the concentrate obtained in step (j) by the addition of such amounts of water and ethanol, if necessary, that a solution with 5 to 20% by weight dry extract in water or not more than 60% by weight aqueous ethanol is obtained;

(l) extracting the aqueous ethanolic solution of step (k) with an aliphatic solvent having a boiling point of 60 to 100° C., separating the aqueous phase from the aliphatic solvent phase to obtain a water phase; and (m) concentrating the water phase obtained in step (l) under reduced pressure and at a temperature of not more than 60 to 80° C. to obtain the dry extract of *Gingko biloba* with a water content of less than 5% by weight;

wherein the dry extract of *Ginkgo biloba* leaves has a content of 22.0% by weight to 27.0% by weight flavonoids, calculated as flavon glycosides; 2.6% by weight to 3.2% by weight bilobalide; 2.8% by weight to 3.4% by weight ginkgolides A, B and C; and not more than 5 ppm ginkgolic acids.

2. The method according to claim 1, wherein as extraction solvent in step (a) acetone containing water having an acetone content of about 50 to 70% by weight is used.

3. The method according to claim 2, wherein as extraction solvent in step (a) acetone containing water having an acetone content of about 60% by weight is used.

4. The method according to claim 1, wherein as extraction solvent in step (a) alkanol containing water, selected from methanol, ethanol, 1-propanol and 2-propanol, having an alkanol content of about 50% by weight to 70% by weight is used.

5. The method according to claim 4, wherein as extraction solvent in step (a) ethanol containing water having an ethanol content of about 60% by weight is used.

6. The method according to claim 1, wherein in step (c) the diluted aqueous solution is cooled to a temperature below 12° C.

7. The method according to claim 1, wherein in step (d) said extraction solvent is a mixture of methyl ethyl ketone and acetone in a ratio of 7/3 to 3/4 (m/m).

8. Method according to wherein in step (i) said extraction solvent is 1-butanol.

9. The method according to claim 1, wherein in step (l) said aliphatic solvent is heptane.

10. The method according to claim 9, wherein the heptane is n-heptane or a mixture of heptane isomers having a portion of more than 35% by weight of n-heptane.

* * * * *